United States Patent [19]

Sano et al.

[11] Patent Number: 4,905,699

[45] Date of Patent: Mar. 6, 1990

[54] METHOD AND APPARATUS FOR NMR IMAGING

[75] Inventors: Koichi Sano, Sagamihara; Tetsuo Yokoyama, Tokyo; Hideaki Koizumi, Katsuta, all of Japan

[73] Assignee: Hitachi, Ltd., Tokyo, Japan

[21] Appl. No.: 92,303

[22] Filed: Sep. 2, 1987

[30] Foreign Application Priority Data

Sep. 3, 1986 [JP] Japan ................................ 61-207055

[51] Int. Cl.$^4$ ............................................... A61B 5/05
[52] U.S. Cl. .................................. 128/653 A; 128/721
[58] Field of Search ....................... 128/653, 721, 716; 324/307, 309

[56] References Cited

U.S. PATENT DOCUMENTS

| 4,567,893 | 2/1986 | Charles et al. | 128/653 |
| 4,604,578 | 8/1986 | Young | 324/307 |
| 4,663,591 | 5/1987 | Pelc et al. | 128/653 |
| 4,682,109 | 7/1987 | Cuppen | 128/653 X |
| 4,694,836 | 9/1987 | Bulkman et al. | 128/653 |
| 4,712,560 | 12/1987 | Schaefer et al. | 128/653 |
| 4,727,882 | 3/1988 | Schneider et al. | 128/721 X |
| 4,730,620 | 3/1988 | Bailes | 128/721 X |

OTHER PUBLICATIONS

Ehman et al, "Magnetic Resonance Imaging with Respiratory Gating", AJR 143, Dec. 1984, pp. 1175–1182.

Primary Examiner—Francis Jaworski
Attorney, Agent, or Firm—Antonelli, Terry & Wands

[57] ABSTRACT

In order to permit the detection of a respiratory motion and an imaging synchronized with the respiration by an NMR imaging apparatus itself without any special hardware, a sequence for detecting the respiratory motion is repeated for a short time immediately before the measurement of an image signal to detect the position and speed of the respiratory motion, and a desired image signal is measured in synchronism with the detected position. Alternatively, the respiratory motion is detected immediately after the measurement of an image signal, and the measured image signal is corrected in accordance with the detected amount to obtain a desired image signal synchronized with the respiration.

9 Claims, 8 Drawing Sheets

F I G. 5
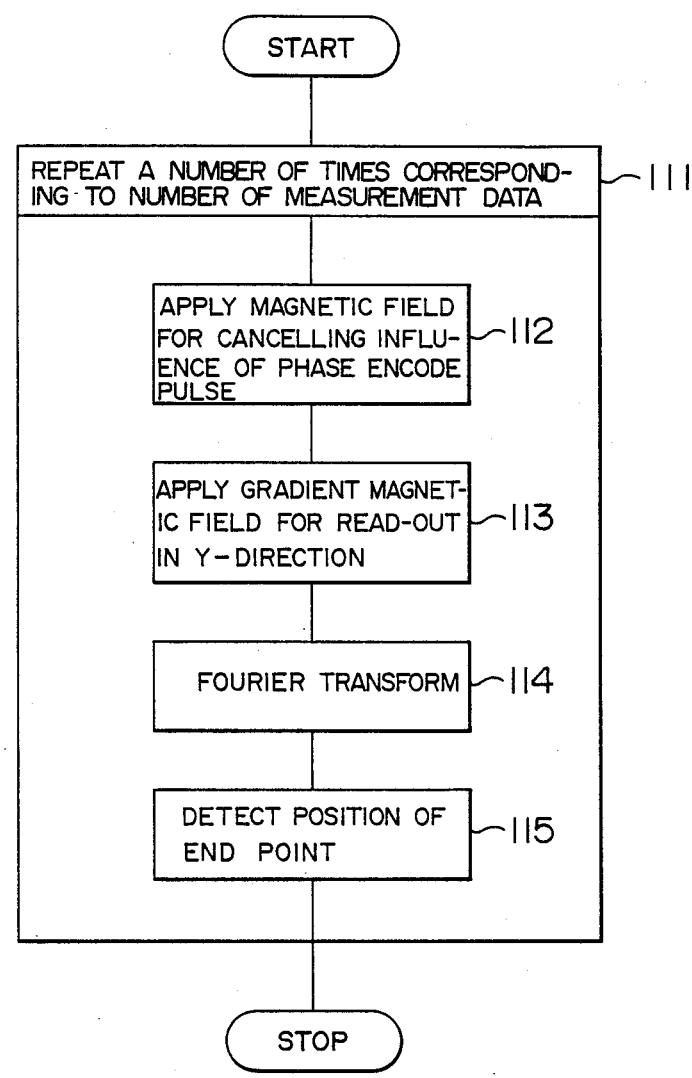

METHOD AND APPARATUS FOR NMR IMAGING

BACKGROUND OF THE INVENTION

The present invention relates to an NMR (Nuclear Magnetic Resonance) imaging or a computed tomography method and apparatus for diagnosis of a body utilizing NMR phenomena, and more particularly to an NMR imaging method and apparatus in which respiratory motion artifacts are reduced.

An NMR imaging apparatus requires a time of about 2 to 20 minutes for imaging. Therefore, the apparatus has a problem that when the breast or abdomen is to be imaged, a blurred image and/or artifacts is produced due to the influence of respiration. In order to avoid this problem, M. L. Wood et al have proposed in "Suppression of respiratory motion artifacts in magnetic resonance imaging", Med. Phys. 13 (6), November/December 1986 (1) a method of detecting a respiratory motion for synchronization therewith and (2) a method of interchanging the order of measurement of data (or the order of application of phase encoding pulses) in accordance with a respiratory motion. However, each of these methods requires the addition of a special hardware exclusively used for detecting the respiratory motion and inhibits efficient operability for performing an imaging. Examples of a method of detecting the respiratory motion include (1) an air bag method in which the respiratory motion is detected utilizing a phenomenon that the pressure in an air bag fixed on the abdomen changes depending on the respiration, (2) a band method in which the respiratory motion is detected utilizing a phenomenon that a tube filled with a solution of zinc sulfate and banded or wound around the abdomen expands depending on the respiration with a change in electric resistance of the tube, and (3) a thermistor method in which a thermistor is attached near the naris to detect a temperature which changes depending on the respiration.

SUMMARY OF THE INVENTION

An object of the present invention made taking the above-mentioned problems into consideration is to provide an NMR imaging method and apparatus in which a respiratory motion is detected by only the NMR imaging apparatus itself without any special hardware to produce an unblurred image synchronized with the respiration.

To that end, according to the present invention, when an imaging is made, information concerning a respiratory motion is measured together with an image signal. More particularly, prior to the imaging or immediately after the measurement of the image signal, a sequence for detecting the respiratory motion is repeated for a short time.

BRIEF DESCRIPTION OF THE DRAWINGS

FIG. 5 is a flow chart showing the operation procedure in the second embodiment of the invention;

DESCRIPTION OF THE PREFERRED EMBODIMENTS

For the purpose of better understanding of the present invention, a sequence for detecting a respiratory motion will first be explained.

Figure 3:
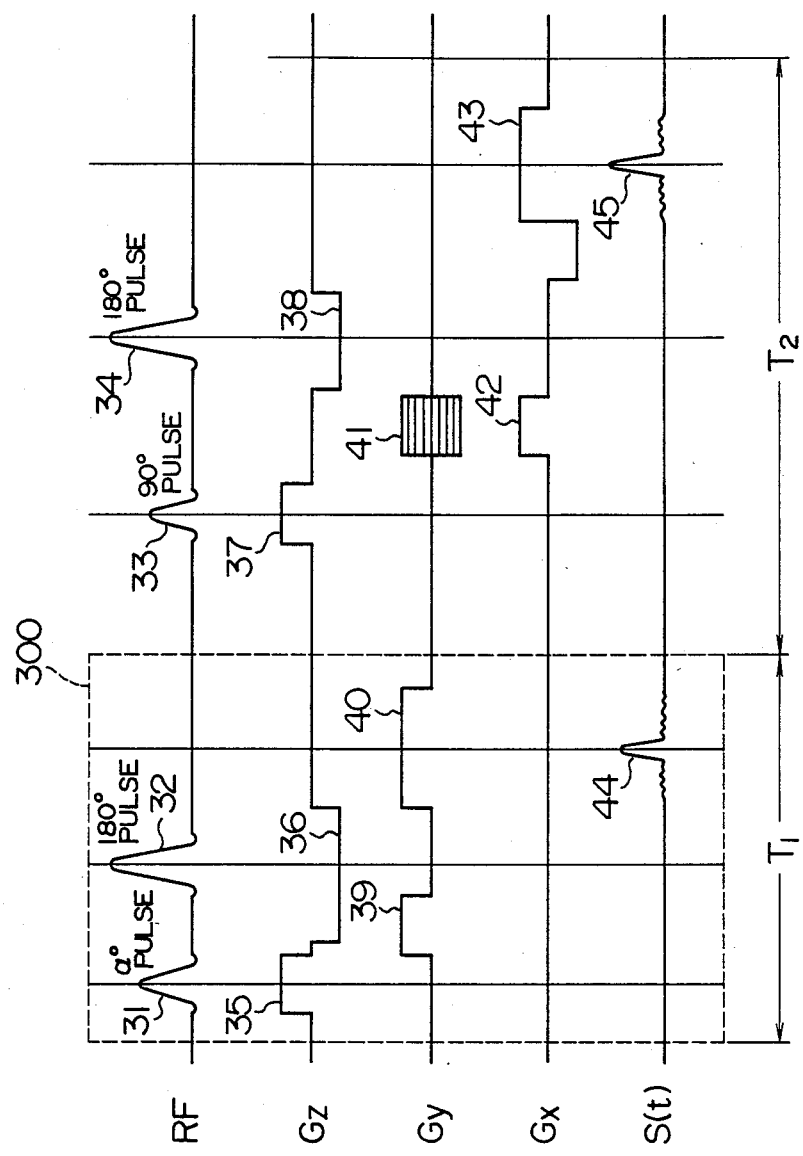
FIG. 3 shows an example of a respiratory motion detecting sequence in the first embodiment of the invention.

FIG. 3 shows an example of the respiratory motion detecting sequence. In this example, the respiratory motion is detected prior to an imaging. Assume that the respiratory motion takes place in a y-direction. A part 300 of FIG. 3 enclosed by dotted line is characteristic of the present invention. The shown sequence is repeated many times for a short time to measure a signal. The measured signal is Fourier-transformed so that the position and speed of the respiratory motion can be derived from amplitude information and phase information, respectively.

An RF pulse 31 is first applied to incline the spin by $\alpha°$ which is 90° to 180°. As the angle $\alpha$ is nearer to 180°, the repetition period can be shortened because of rapid relaxation but a signal measured becomes small. Thereafter, a 180° pulse 32 is applied and a signal 44 is measured while applying a gradient magnetic field (Gy) 40 in a y-direction. The position and speed of the respiratory motion are detected from the signal 44 to check whether or not a predetermined timing at which an imaging is to be performed in synchronism with the respiration is reached. When a deviation from the predetermined timing exists, the above-mentioned sequence is repeated until the predetermined timing is obtained.

The detection of a condition or status of the respiration is based on a principle which will be described hereinbelow.

Data obtained by the Fourier transform of the signal 44 measured is data in which the image signal is projected onto the y-axis. The amplitude of the image signal results in the projection value and the phase thereof results in a value proportional to the speed of movement of each projection data in the y-direction. Accordingly, the position of the respiratory motion can be determined by detecting the position of an end point of the projection data while the speed thereof can be determined from the phase value. For example, if the sequence enclosed by dotted line 300 in FIG. 3 is repeated in units of 100 msec, the position and speed of the respiratory motion can be detected with a lag of at largest 100 msec. The condition of respiration can be extracted from information concerning a slice adjacent a slice of the object for which an NMR signal for imaging is measured.

The condition of the respiration can be also detected from the amount of protons in a cross section or slice instead of the position and speed. This method utilizes a fact that the respiratory motion involves a movement in or parallel to the cross section as well as a movement perpendicular to the cross section. An integration of projection values is calculated to provide the total amount of hydrogen protons included in the cross section. The condition of the respiration can be detected from a variation of the total amount of protons.

The present invention will now be described with reference to embodiments.

Figure 2:
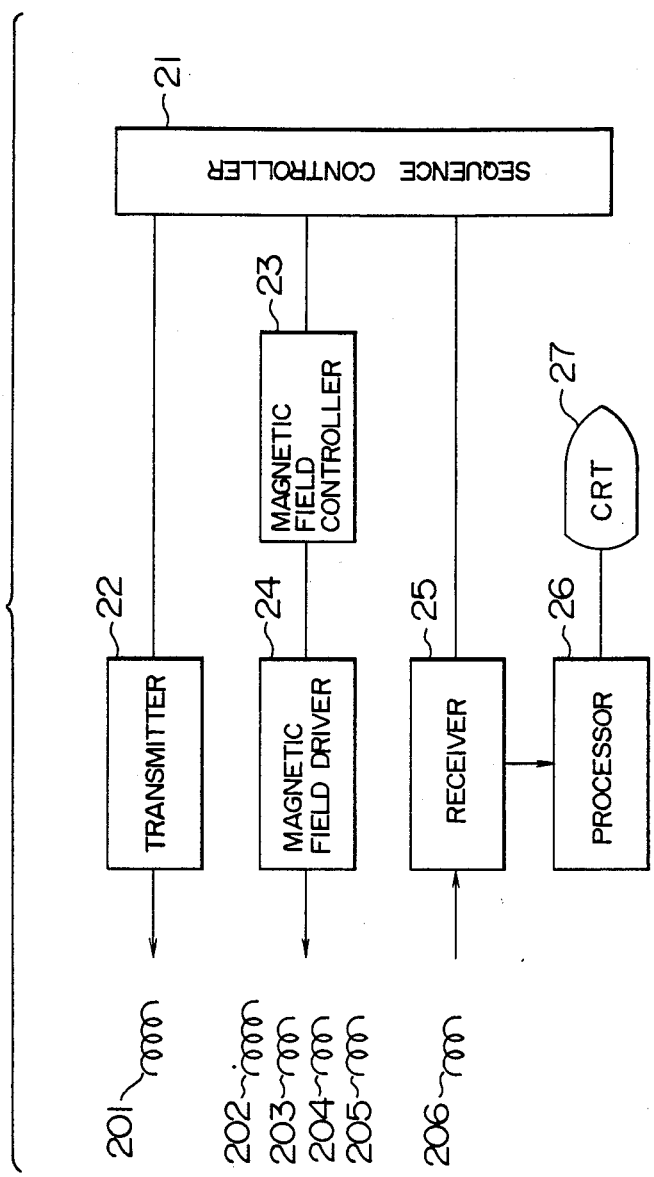
FIG. 2 shows a block diagram of an NMR imaging apparatus employing the present invention.

FIG. 2 is a block diagram of an NMR imaging apparatus according to an embodiment of the present invention. A sequence controller 21 has a function of controlling various pulses and magnetic fields generated for detecting NMR signals from an object. The sequence controller 21 controls a high frequency pulse transmitter 22 which has a function of driving a coil 201 to generate high frequency pulses for causing a specific nuclide of the object to resonate, a magnetic field controller 23 which has a function of driving a coil 202 to generate a static magnetic field determining a resonance frequency of the NMR signal and coils 203, 204 and 205 to generate gradient magnetic fields in x-, y- and z-directions the magnitudes and directions of which are arbitrarily controllable, and a receiver 25 which has a function of receiving the NMR signal generated from the object by a coil 206 and performing the measurement of the NMR signal after detection thereof. A processor 26 takes in the measured signal from the receiver 25 to perform image reconstruction and various operations based thereon. The reconstructed image is displayed on a CRT display 27.

Figure 1:
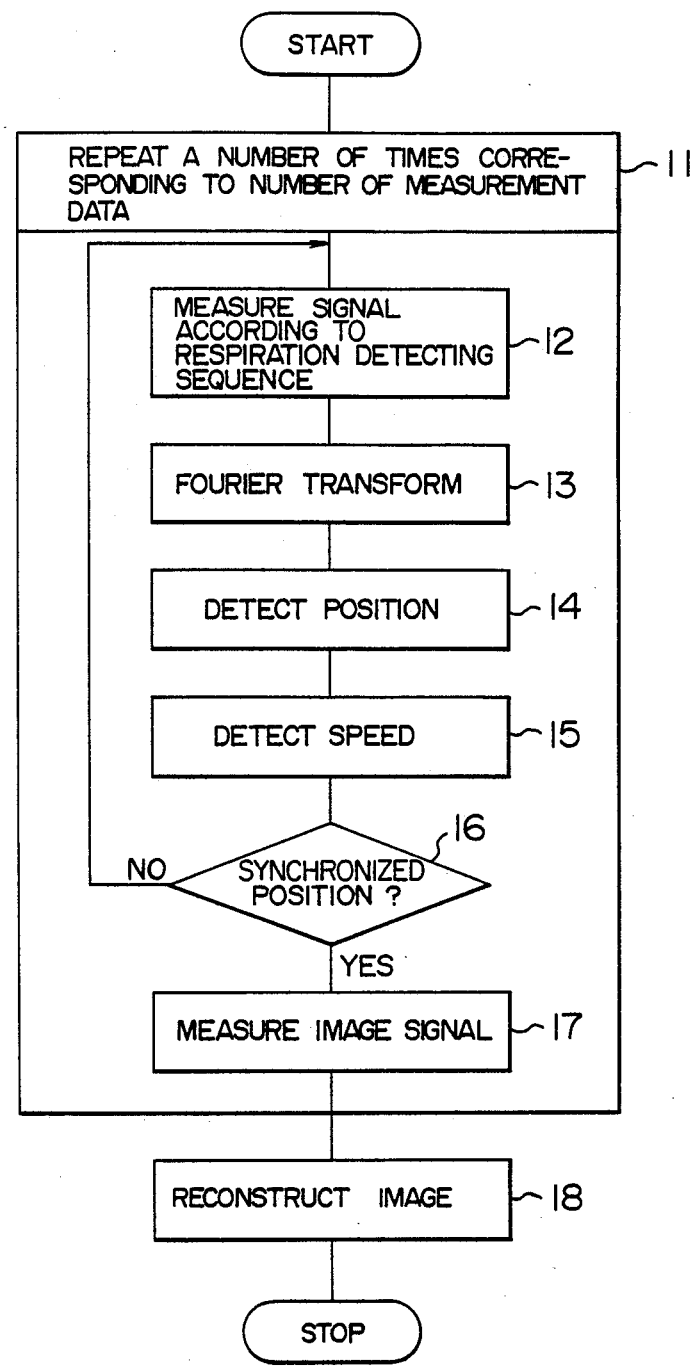
FIG. 1 is a flow chart showing the operation procedure in a first embodiment of the present invention.

Next, the operation of the first embodiment of the present invention having the above-described construction will be explained referring to a flow chart of the operation procedure shown in FIG. 1 and the example of pulse sequence shown in FIG. 3. Though the following explanation is made in conjunction with the case where a respiratory motion takes place in the y-direction, the explanation may be applicable even in the case where the respiratory motion takes place in any direction.

Step 11: In the sequence shown in FIG. 3, a step 12 (a section $T_1$ in FIG. 3) and steps 13 to 17 (a section $T_2$ in FIG. 3) are repeated by the number n of measurement data (n=256 in a usual case) required for image reproduction while successively changing the amplitude of a phase encoding pulse 41. An image signal is measured along the following sequence.

Step 12: A signal 44 is measured in accordance with the sequence for detecting the respiration having its motion in the y-direction. Namely, a $\alpha°$ pulse 31 ($90 \leq \alpha < 180$) and a 180° pulse 32 are applied together with gradient magnetic fields ($G_z$) 35 and 36. Upon signal measurement, a gradient magnetic field ($G_y$) 40 is applied. It is of course that a gradient echo method may be employed in which a signal is measured by setting the angle $\alpha$ to a small value and inverting the polarity of the gradient magnetic field ($G_y$) 40 instead of the use of the 180° pulse 32.

Step 13: The measurement signal 44 [S(t)] is Fourier-transformed and the amplitude [A(y)] and phase [$\theta$(y)] of data [P(y)] after the Fourier transform are determined from the following equation:

$$P(y) = \theta[S(t)] = A(y) \exp[j\theta(y)]$$

Step 14: Since the amplitude A(y) is data (e.g. 133 in FIG. 6) of projection of the image signal onto the y-axis, the position of an end point (e.g. a point 91 in FIG. 6) of the projection data giving A(y)=0 is detected.

Step 15: Since the phase $\theta$(y) shows a speed on each y-coordinate point of the projection data, a speed v(y) in the y-direction is calculated from the following equation showing a relation between the speed and the phase:

$$\theta(y) = \gamma G t_p t_I v(y)$$

Here, $\gamma$ is the nuclear magnetic rotation ratio, G the magnitude of pulses 39 and 40, $t_p$ the time of duration of a pulse 39, $t_I$ the interval between the application start instants of the time of the pulses 39 and 40, and v(y) the speed of a moving part in a flow encode direction.

Step 16: Whether or not a predetermined timing of the respiration at which the imaging is to be made is reached, is checked from the detected position or speed or the detected position and speed. For example, if it is desired to conduct the imaging at the timing of expiration, i.e. at a point of time when the breathing-out becomes the maximum, a point of time is detected at which an end point of the projection data takes the lowest position and a speed of the end point becomes zero. The imaging is made at the detected timing. In that case, the detection of such a timing can be made by use of either one of the position and speed. If the predetermined timing is not reached, the process is returned to the step 12 to repeat the steps 12 to 15. A certain suitable interval of time is provided before carrying out the steps 12 to 15 again since an immediate repetition without delay yields no signal because of the presence of a relaxation time. When the predetermined timing is obtained, the process proceeds to a step 17.

Step 17: The imaging is effected in accordance with a usual pulse sequence to measure an image signal 45.

Step 18: The image reproduction is effected on the basis of the image signals 45 obtained repeatedly in synchronism with the respiration.

Since the image obtained through the above mentioned procedure is synchronized with the respiration, an image of high quality free of image deterioration such as moving artifacts associated with the respiratory motion of a patient can be produced.

According to the above embodiment, there is provided an effect that the detection of the respiratory motion and the synchronization with the respiration can be achieved by only the NMR imaging apparatus itself without any special hardware and hence image of high quality can be obtained in a simple and economical manner.

Figure 4:
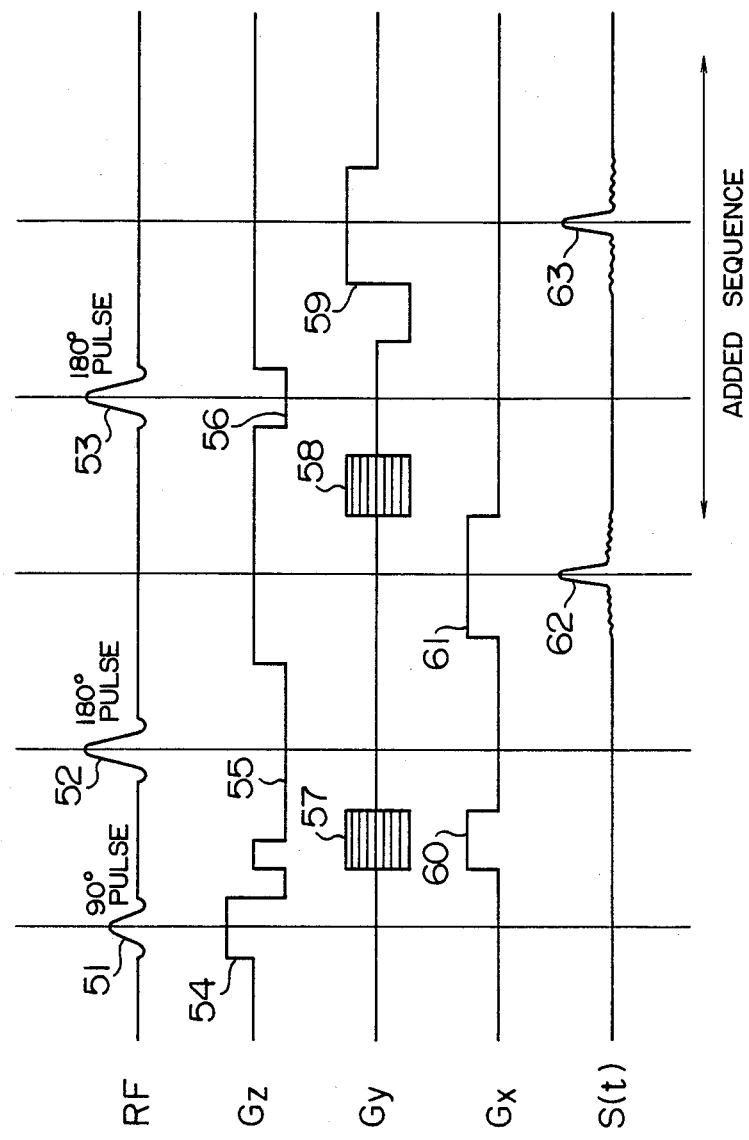
FIG. 4 is a sequence of pulses for explaining the principle of a second embodiment of the present invention.

FIG. 4 shows a pulse sequence for explaining the principle of a second embodiment of the present invention. Though in the first embodiment the signal for detecting the respiratory motion is measured prior to the imaging, in the second embodiment a signal including information concerning the respiratory motion is measured immediately after an image signal has been measured. In the second embodiment, a sequence indicated by an arrow in FIG. 4 is added.

Referring to FIG. 4, a phase encoding pulse 58 cancels the influence of a gradient magnetic field of the preceding phase encoding pulse 57 just therebefore upon the spin and a gradient magnetic field (Gy) 59 for read-out is applied in the y-direction. A signal 63 observed at that time is Fourier-transformed to provide an image signal projected onto the y-axis. A position of the respiratory motion or a current condition or status of the respiration can be sensed in accordance with whether the position of an end point of the projected image signal is at an upper position in a changing region or at a lower position therein.

The operation of the second embodiment using the pulse sequence shown in FIG. 4 will now be explained along a flow chart of operation procedure which is shown in FIG. 5 and can be realized by the apparatus having the construction shown in FIG. 2.

Step 111: In the pulse sequence shown in FIG. 4, while successively changing the amplitude of a phase encoding pulse 57, a signal 63 for position detection is measured by the number of measurement data required for image reproduction in accordance with the following sequence.

Step 112: A pulse 58 having the same amplitude as the phase encoding pulse 57 is applied to cancel the influence of the pulse 57. The cancellation of the influence of the pulse 57 by the pulse 58 is possible since a 180° pulse 52 is applied.

Step 113: A gradient magnetic field (Gy) 59 for readout in the y-direction is applied to measure the position detection signal 63.

Step 114: The measurement signal 63 is Fourier-transformed to produce data (see FIG. 6) projected onto the y-axis.

Step 115: An upper end point 91 of the projection data is detected. A position of the respiration, i.e. a current condition or status of the respiration can be detected in accordance with whether the upper end point 91 of each projection data is at an upper position in a changing region or at a lower position therein.

Figure 6:
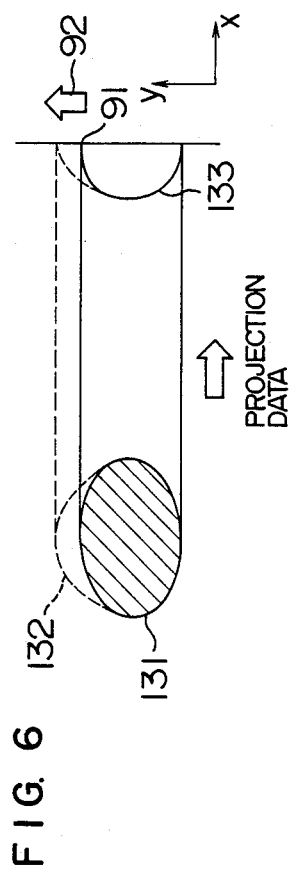
FIG. 6 is a view for explaining a general concept of the sequence shown in FIG. 4.

FIG. 6 shows the distribution of an image signal 133 which is data projected onto the y-axis through the Fourier transform of the signal 63 measured by the sequence shown in FIG. 4. From the position 91 of an end point of the image signal 133 can be determined a condition of the respiration at each of points on the y-axis moving in a direction indicated by arrow 92. In FIG. 6, a hatched portion 131 shows a tomographic or cross section image at the time of breathing-out and a portion 132 enclosed by dotted line and including oblique lines shows a tomographic image at the time of breathing-in.

Next, as a third embodiment of the present invention will be explained a method in which an image signal measured is corrected on the basis of information concerning the respiratory motion which information is measured immediately after the image signal has been measured.

Figure 7:
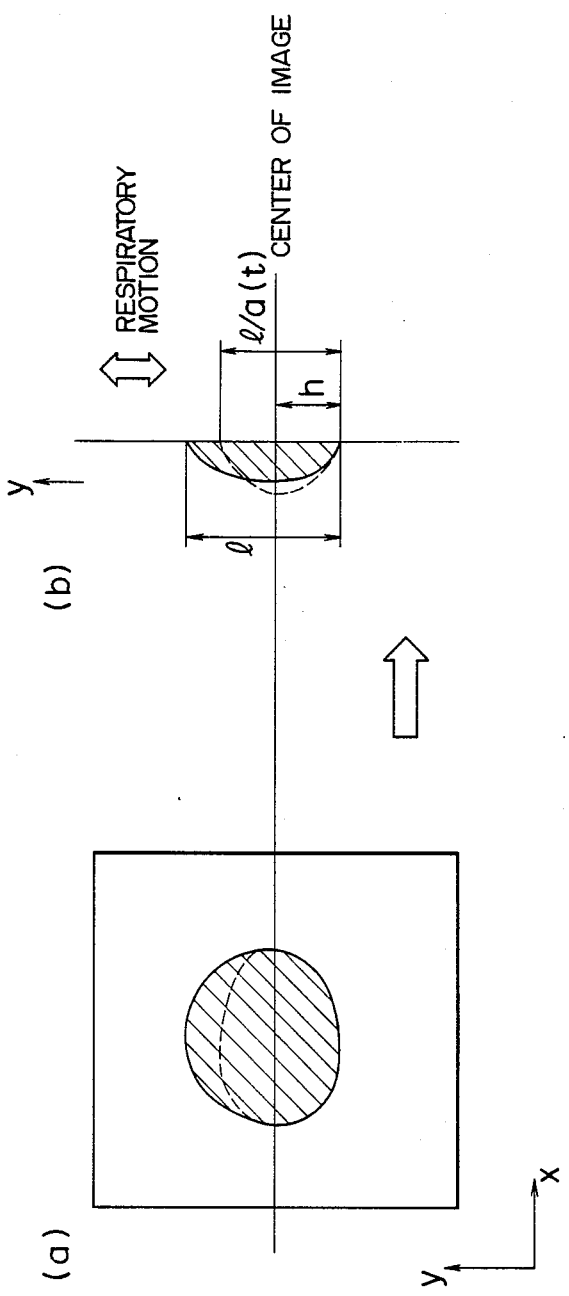
FIG. 7 is a view for explaining parameters necessary for correction of a respiratory motion.

The principle of correction for a detection signal will be first explained referring to FIG. 7. Now assume that the respiratory motion taken place in only the y-direction, as is shown in (a) of FIG. 7. Therefore, the following explanation is made in terms of one-dimensional data.

Provided that a shaded portion in (a) of FIG. 7 is a state in which the abdomen expands most greatly upon breathing-in, projection data at that time has a profile shaded in (b) of FIG. 7. A distance between upper and lower ends of the shaded projection data is represented by l and a distance between the image center and the lowermost end is represented by h. A state of breathing-in at any given instant of time t is shown by dotted line and a distance between upper and lower ends of projection data at the instant of time t is l/a(t). Namely, a(t) corresponds to the coefficient of contraction Assuming that a measurement signal corresponding to the shaded projection data (or Fourier spectrum of projection data) is F(ω), a measurement signal G(ω) of the portion shown by dotted line is expressed by the following equation (1).

$$G(\omega) = F\left(\frac{\omega}{a(t)}\right) e^{-jh(1-\frac{1}{a(t)})\omega} \quad (1)$$

Accordingly, if the values of variables a(t) and h in the equation (1) are known, F(ω) can be determined from the measurement signal G($\frac{\omega}{a}$). This process includes a process of correcting from the equation (1) a phase change of $$e^{-jh(1-\frac{1}{a(t)})\omega} \quad (2)$$

and a resampling process of determining F(ω) from $$F\left(\frac{\omega}{a(t)}\right).$$

Namely, the correction is possible if h and a(t) are determined. The value of h can be readily determined by carrying out a usual image reproduction while the value of a(t) can be measured by the sequence of FIG. 4 mentioned above.

Figure 8:
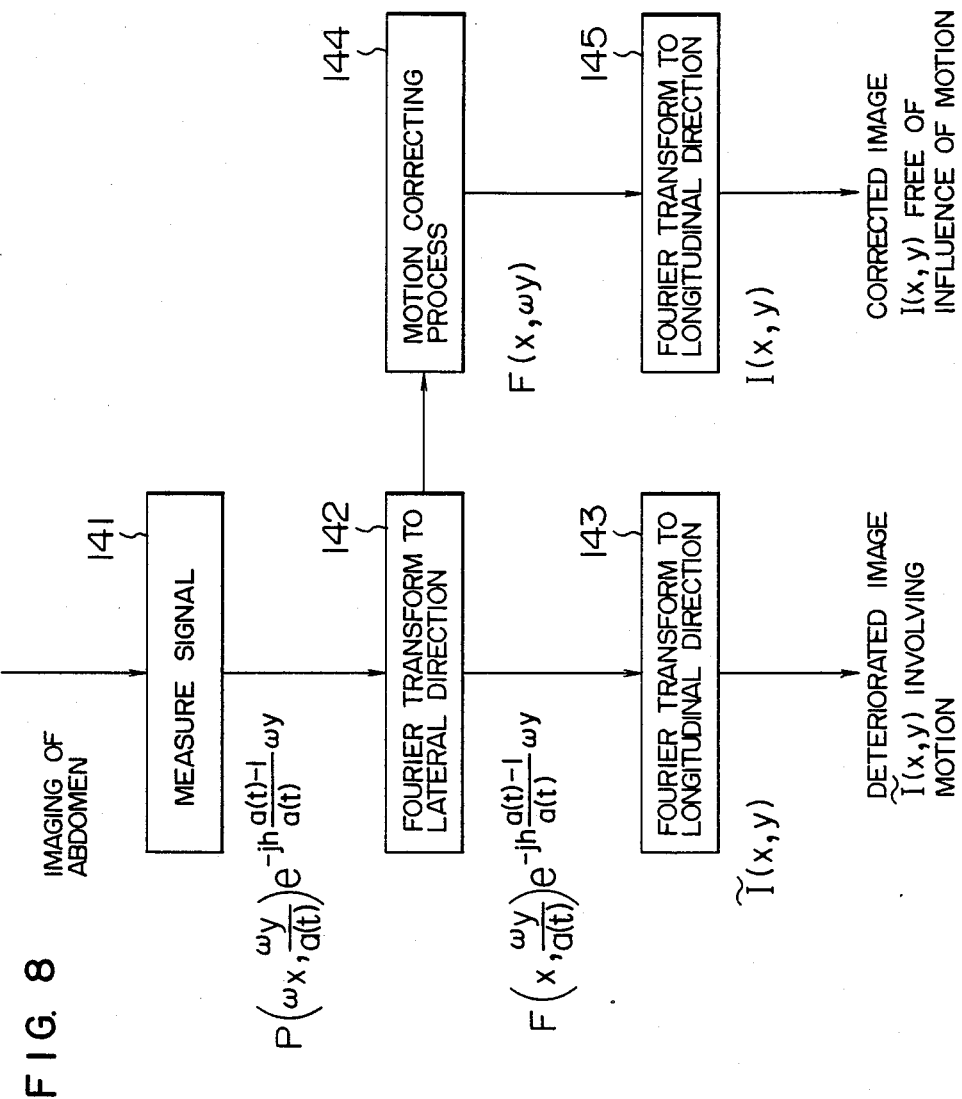
FIG. 8 is a flow chart showing a general concept of the processing in a third embodiment of the present invention.

The above procedure is shown in a flow chart of FIG. 8 in terms of signal levels in actual image measurement. Providing that the motion exists in only the y-direction, a measurement signal obtained by the imaging of the abdomen at a block 141 is as follows:

$$P\left(\omega_x, \frac{\omega_y}{a(t)}\right) e^{-jh\frac{a(t)-1}{a(t)}\omega_y} \quad (3)$$

Since no motion in the x-direction is present, a Fourier transform to a lateral direction at a block 142 provides:

$$F\left(x, \frac{\omega_y}{a(t)}\right) e^{-jh\frac{a(t)-1}{a(t)}\omega_y} \quad (4)$$

In a usual case, a Fourier transform to a longitudinal direction is immediately made at a block 143 to obtain an image I(x, y). But, this image involves the influence of the motion and hence the quality of the image is deteriorated. On the other hand, according to the present embodiment of the invention, after the Fourier transform to the lateral direction, a motion correcting process including phase correction and resampling is performed at a block 144 to produce a measurement signal F(x, ω_y) involving no motion and thereafter a Fourier transform to a longitudinal direction is carried out at a block 145 to produce an image I(x, y) in which the influence of the motion is corrected.

Figure 9:
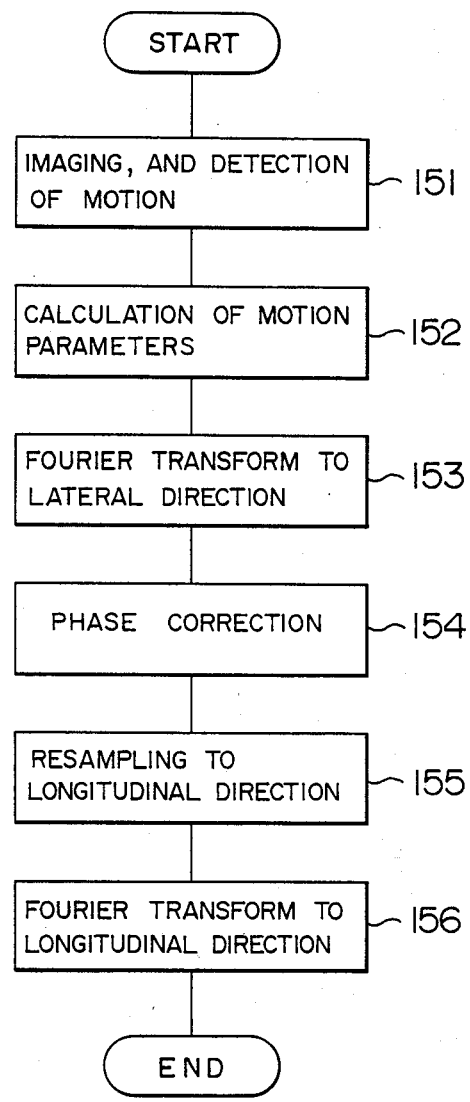
FIG. 9 is a flow chart showing the operation procedure in the third embodiment of the invention.

Further detailed explanations will now be made in virtue of a concrete example along a flow chart of operation procedure which is shown in FIG. 9 and can be realized by the apparatus shown in FIG. 2.

Step 151: In the pulse sequence shown in FIG. 4, an image measurement signal 62 and a position detection signal 63 are measured by the number of measurement data required for image reproduction while successively changing phase encoding pulses 57 and 58.

Step 152: The parameter h shown in (b) of FIG. 7 is determined on the basis of an image reproduced from the image measurement signal 62 obtained at the step 151 as it is. Also, the position detection signal 63 is Fourier-transformed to produce data of projection to the y-axis upon each signal measurement, thereby determining the length l at the state of most breathing-in. The values of a(t) at respective measurement instants of l are determined from the determined value of l. In this manner, the values of parameters h, l and a(t) necessary for correction are obtained.

Step 153: The measurement signal is Fourier-transformed to the lateral direction to produce a signal shown by the above expression (4).

Step 154: For each measurement signal, the values of a(t) and h are used to determine the value of the following expression (5):

$$e^{jh \frac{a(t)-1}{a(t)} \omega y} \quad (5)$$

The determined value of the expression (5) is multiplied by the value of the expression (4), thereby obtaining a phase-corrected signal expressed as follows:

$$F\left(x, \frac{\omega_y}{a(t)}\right) \quad (6)$$

Step 155: A process of resampling to the $\omega_y$-axis direction which is the longitudinal direction is carried out based on the value of the expression (6), thereby obtaining the value of the following expression (7):

$$F(x, \omega_y) \quad (7)$$

Any interpolation method can be employed for the resampling process. For example, linear interpolation or spline interpolation may be applicable.

Step 156: A Fourier transform to the longitudinal direction for the expression (7) subjected to the phase correcting process and the resampling process, thereby obtaining an image in which the influence of the respiratory motion is eliminated.

According to the third embodiment of the present invention, there is provided an effect that the detection of the respiratory motion upon signal measurement can be detected by only the NMR imaging apparatus itself without any special hardware and an image of high quality can be economically obtained without a need of synchronization with the respiration.

As has been mentioned above, according to the present invention, information concerning a respiratory motion is measured together with an image signal. Therefore, the respiratory motion can be detected by only an NMR imaging apparatus itself so that the influence of the respiratory motion is corrected.

We claim:

1. An NMR imaging method comprising:
   a process of generating magnetic fields for application to an object for production of NMR signals;
   a process of producing a plurality of first NMR signals representative of information concerning respiratory motion of said object including at least one of position information of the respiration, speed information of the respiration, and information representative of an integration of the first NMR signals, and a second NMR signal representative of image information concerning an internal structure of said object is accordance with the generated fields;
   A process of measuring the produced first NMR signals including repeatedly measuring the first NMR signals at a predetermined time interval and extracting from the repeatedly measured first NMR signals a timing at which the respiration assumes the same condition of respiratory motion, and a step of measuring the second NMR signal in synchronism with the respiratory motion on the basis of the extracted information; and
   a process of performing image reconstruction in accordance with the measured second NMR signal.

2. An NMR imaging method according to claim 1, wherein said step of extracting said information concerning the respiratory motion includes extracting information concerning a slice adjacent to a slice of the object for which the second NMR signal is measured.

3. An NMR imaging method according to claim 1, wherein said information concerning respiratory motion includes said position information concerning data projected to a direction perpendicular to a direction at which the respiratory motion is to be measured.

4. An NMR imaging method according to claim 1, wherein said information concerning the respiratory motion includes said speed information and a corresponding of said speed information is made to phase information of the first NMR signals.

5. An NMR imaging method according to claim 1, wherein the process of producing the first and second NMR signals utilizes the same apparatus for yielding the NMR signals thereby enabling imaging of the object with respiratory motion artifacts being reduced and without special hardware exclusively utilized for detecting the respiratory motion.

6. An NMR imaging method according to claim 1, wherein the second NMR signal is measured at the timing at which the respiration assumes the same condition of the respiratory motion.

7. An NMR imaging apparatus comprising:
   means for yielding NMR signals of an object including means for generating and applying magnetic fields to the object;
   means for producing at least one first NMR signal representative of information concerning a respiratory motion of the object and a second NMR signal representative of image information concerning an internal structure of the object in accordance with the generated magnetic fields utilizing the same means for yielding the NMR signals;
   means for extracting the information concerning the respiratory motion from the produced first NMR signal;
   means for measuring the second NMR signal in synchronism with the respiratory motion on the basis of the extracted information; and
   means for performing image reconstruction in accordance with the measured second NMR signal.

8. An NMR imaging apparatus according to claim 7, wherein said means for producing at least one first NMR signal representative of information concerning a respiratory motion of the object includes means for producing a plurality of first NMR signals including at least one of position information of the respiration, speed information of the respiration, and information representative of an integration of the first NMR signals, and said means for extracting the information concerning the respiratory motion from the produced first NMR signal includes means for extracting the information from the produced first NMR signals including means for repeatedly measuring the first NMR signals at a predetermined time interval and extracting from the repeatedly measured first NMR signals a timing at which the respiration assumes the same condition of respiratory motion.

9. An NMR imaging apparatus according to claim 8, wherein said means for measuring the second NMR signal effects measurement at the timing at which the respiration assumes the same condition of the respiratory motion.

* * * * *